United States Patent [19]

Ueyama

[11] Patent Number: 5,204,629
[45] Date of Patent: Apr. 20, 1993

[54] AUTOMATIC ALIGNING MECHANISM FOR NUCLEAR MAGNETIC RESONANCE IMAGING APPARATUS

[75] Inventor: Akihide Ueyama, Tochigi, Japan

[73] Assignee: Kabushiki Kaisha Toshiba, Kawasaki, Japan

[21] Appl. No.: 620,777

[22] Filed: Dec. 3, 1990

[30] Foreign Application Priority Data

Dec. 4, 1989 [JP] Japan ............................ 1-314554

[51] Int. Cl.⁵ .............................................. G01V 3/00
[52] U.S. Cl. .................................. 324/318; 324/322; 128/653.5
[58] Field of Search .................. 324/318, 322, 307; 128/653.5; 378/209

[56] References Cited

U.S. PATENT DOCUMENTS

| | | | |
|---|---|---|---|
| 4,629,989 | 12/1986 | Riehl et al. | 324/318 |
| 4,727,328 | 2/1988 | Carper et al. | 324/318 |
| 4,771,785 | 9/1988 | Duer | 324/318 |
| 5,066,915 | 11/1991 | Omori et al. | 324/318 |

*Primary Examiner*—Louis Arana
*Attorney, Agent, or Firm*—Foley & Lardner

[57] ABSTRACT

An automatic aligning mechanism is used for a nuclear magnetic resonance imaging apparatus, the imaging apparatus producing an image of a section of an inspected portion of a subject at a predetermined inspecting position in a central space of a main coil supported by a gantry, by means of the principles of nuclear magnetic resonance. The mechanism includes a base having a table top, on which the subject is placed and which is movable to move the subject into and out from on opening of the gantry corresponding to the inner space of the main coil, a position measuring unit, having an indicating member which is movable on the top to indicate an inspected portion of the subject and measuring a relative position of the inspected portion to the top by the moving distance of the indicating member, and a detecting unit, which detects a distance between the subject's inspected portion and a predetermined inspecting position in the central space of the main coil on the basis of the measured result by the position measuring unit and moves the plate for the detected distance toward the gantry's opening.

12 Claims, 2 Drawing Sheets

AUTOMATIC ALIGNING MECHANISM FOR NUCLEAR MAGNETIC RESONANCE IMAGING APPARATUS

BACKGROUND OF THE INVENTION

1. Field of the Invention

The present invention relates to a nuclear magnetic resonance imaging apparatus for obtaining an image of a section of an inspected portion of a subject by means of the principle of nuclear magnetic resonance and, more particularly, to an automatic aligning mechanism used to automatically align the inspected portion of the subject at an inspecting position of the imaging apparatus.

2. Description of the Related Art

As shown in FIG. 1, a conventional nuclear magnetic resonance imaging apparatus has a gantry 16 which supports a hollow-shaped main coil 12, a hollow-shaped gradient coil 14 coaxially disposed in the hollow region of the hollow-shaped main coil 12, and a transmitting-/receiving coil 15. The main coil 12 is used for applying a static magnetic field to a subject 10, such as a patient, located in its hollow region 1, the gradient coil 14 is used for generating a gradient magnetic field to obtain position information of a portion, at which a nuclear magnetic resonance signal is induced, in the patient 10 located in the static magnetic field 1, and the transmitting/receiving coil 15 is used for transmitting/receiving the nuclear magnetic resonance signal from the inspected portion of the patient 10. The gantry 16 is mounted, for example, on a floor of a hospital.

The gantry 16 has an opening 18 corresponding to the hollow region of the main coil 12 and the gradient coil 14, and the subject 10 is inserted into the opening 18 of the gantry 16 so that the subject 10 is located in the hollow region of the main coil 12 and the gradient coil 14.

The nuclear magnetic resonance imaging apparatus has a bed 20 for inserting the subject 10 into the opening 18 of the gantry 16.

The bed 20 is disposed in the vicinity of the opening 18 on the extension line of the opening 18 of the gantry 16 on the floor, and has a table top 22 being movable along the extension line. The bed 20 can move the table top 22 in upward and downward directions so that the patient 10 can easily ride on or get down from the table top 22.

A light projector 24 extending above the extension line is mounted on the gantry 16 at the side of the bed 20.

In order to obtain an image of a section of an inspected portion 10a of the patient 10 by means of the principle of a nuclear magnetic resonance in the above-mentioned conventional apparatus, the patient 10 is first laid at a predetermined position on the upper surface of the table top 22 in a state that the patient 10 is directed upward, and the table top 22 is set at the same vertical level as the center line of the opening 18 of the gantry 16.

Then, the table top 22 is moved toward the opening 18 of the gantry 16 until a light beam 26 projected downward from the light projector 24 projects onto the inspected portion 10a of the patient 10 laid on the upper surface of the table top 22. When the inspected portion 10a of the patient 10 is completely aligned to the light beam 26 from the light projector 24, the movement of the table top 22 in a direction along the extension line is stopped temporarily.

A center line 30 in the longitudinal direction of the main coil 12 is an inspecting position in the abovementioned apparatus. After the alignment of the inspected portion 10a of the patient 10 with respect to the light beam 26 from the light projector 24 is finished, the movement of the table top 22 is restarted. The table top 22 is moved along the extension line into the opening 18 for a predetermined distance in a direction along the extension line between the inspecting position 30 and the light projector 24, and automatically stopped. By the restarting and the stop, following the restarting, of the movement of the table top 22, the inspected portion 10a of the patient 10 laid on the upper surface of the table top 22 is brought into coincidence with the inspecting position 30 in the above-described apparatus as shown in FIG. 2.

Thereafter, when the above-mentioned apparatus performs a predetermined operation necessary to obtain a nuclear magnetic resonance image, a section of the inspected portion 10a of the patient 10 is imaged in the above-described apparatus by means of the principle of nuclear magnetic resonance, the image is displayed on a display (not shown) of the above-mentioned apparatus, and recorded in a recorder (not shown) of the apparatus as required.

When a desired image of the section of the inspected portion 10a is obtained, the table top 22 is returned to its initial position located outside the opening 18 of the gantry 16 without being stopped, and the patient 10 on the table top 22 may get down from the upper surface of the table top 22 at the initial position.

In the conventional nuclear magnetic resonance imaging apparatus constructed and operated as described above, the table top 22 must be temporarily stopped so that the inspected portion 10a of the patient 10 is brought into coincidence with the light beam 26 from the light projector 24. The table top 22 is moved from the initial position of the table top 22, located outside the opening 18 of the gantry 16 and at which the patient 10 is laid at a predetermined portion on the upper surface of the table top 22, into the opening 18 of the gantry 16, and is stopped at a position in which the inspected portion 10a of the patient 10 on the upper surface of the table top 22 is brought into coincidence with the inspecting position 30 in the above-described apparatus. Further, in order to accurately bring the inspected portion 10a into coincidence with the light beam 26 from the light projector 24, the moving speed of the table top 22 must be decelerated as the inspected portion 10a approaches the light beam 26.

Therefore, in the above-mentioned conventional nuclear magnetic resonance imaging apparatus, the abovedescribed temporary stop of the table top 22 and the deceleration of the moving speed of the table top 22 in the vicinity of the temporary stop are both necessary while the table top 22 is moved from the initial position to the inspecting position. However they disturb the shortening of a time required to complete the procedures during which the patient 10 is laid at a predetermined position on the upper surface of the table top 22 at the initial position, the inspected portion 10a of the patient 10 is brought into coincidence with the inspecting position 30 in the abovedescribed apparatus, the section of the inspected portion 10a is imaged, and the table top 22 is returned to the initial position.

The aligning work of the inspected portion 10a with respect to the light beam 26 is troublesome in that it generates a spiritual stress of operator of the abovedescribed apparatus.

In the operation of the expensive nuclear magnetic resonance imaging apparatus, the more the number of patients which are inspected per unit of time, the better. The above-described circumstances in the conventional nuclear magnetic resonance imaging apparatus disturbs the intention to improve the number of the patients to be inspected per unit of time.

SUMMARY OF THE INVENTION

Accordingly, it is an object of the present invention to provide an automatic aligning mechanism for a nuclear magnetic resonance imaging apparatus which can shorten a period of time required to complete the procedures during which a patient to be inspected is laid at a predetermined position on the upper surface of a table top at an initial position, an inspected portion of the patient is then brought into coincidence with an inspecting position in the abovedescribed apparatus and imaged, and the table top is then returned to the initial position, and facilitate an operation thereof.

In order to achieve the above-described object, the automatic aligning mechanism for the nuclear magnetic resonance imaging apparatus according to the present invention including a gantry which supports a main coil, having a central space into which a subject is inserted and generating a static magnetic field to the subject inserted into the central space, and a gradient coil, generating a gradient magnetic field for producing position information of a portion of the subject induced with a nuclear magnetic resonance signal in the static magnetic field, the imaging apparatus producing an image of a section of the subject at a predetermined inspecting position in the central space of the main coil on the basis of the nuclear magnetic resonance signal from the portion of the subject, comprises: a table top supporting base having a table top on which the subject is placed and which is movable to move the subject into and out from the opening of the gantry; means for measuring a position of an inspected portion of the subject on the table top; means for detecting a distance between the inspected portion of the subject and a predetermined inspecting position in the central space of the main coil on the basis of the measured result by the position measuring means and for moving the table top for the detected distance toward the opening of the gantry.

In the automatic aligning mechanism for the nuclear magnetic resonance imaging apparatus characterized by being constructed as described above, when the subject is placed on the table top and the table top is started to be moved toward the opening of the gantry, the movement of the table top is not temporarily stopped until the table top makes the inspected portion of the subject to be brought into coincidence with the predetermined inspecting position in the central space of the main coil.

Therefore, the time described in the object of the present invention can be shortened.

In the mechanism of the present invention, the position of the inspected portion of the subject on the table top is measured by the position measuring means before the movement of the table top toward the opening of the gantry is started.

The measuring of the position without the movement of the table top having relatively large mass is facilitated, and is finished much more quickly in comparison to the conventional apparatus described above.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention, and together with the general description given above and the detailed description of the preferred embodiment given below, serve to explain the principles of the invention.

DETAILED DESCRIPTION OF THE PREFERRED EMBODIMENTS

An embodiment of the present invention will now be described in detail with reference to FIGS. 3 and 4.

Figure 1:
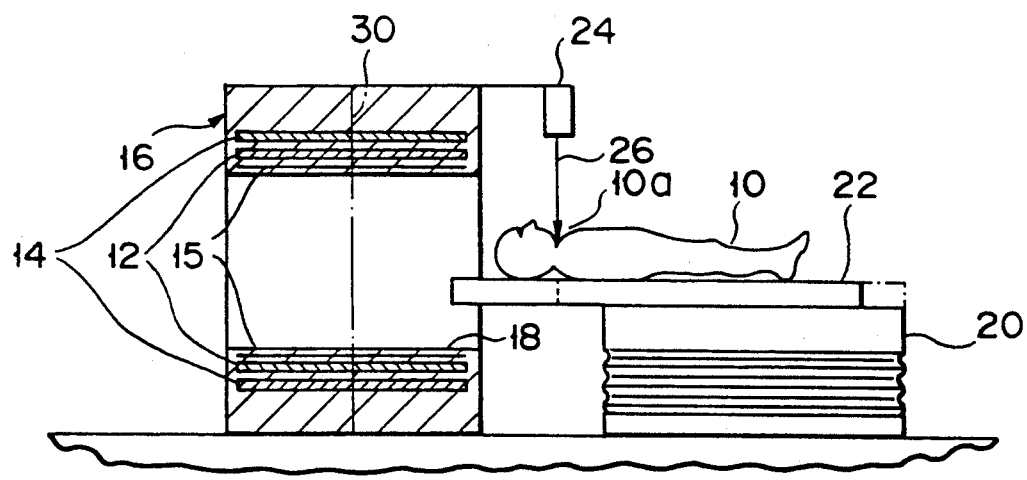
FIG. 1 is a side view schematically showing a conventional automatic aligning mechanism used in a nuclear magnetic resonance imaging apparatus in which a table top of a bed has already moved from an initial position, where a patient to be inspected rides on and gets down from the table top, so that an inspected portion of the patient on the table top is brought into coincidence with a light beam projected from a light projector of the apparatus as a preparing stage of an automatic alignment.
Figure 2:
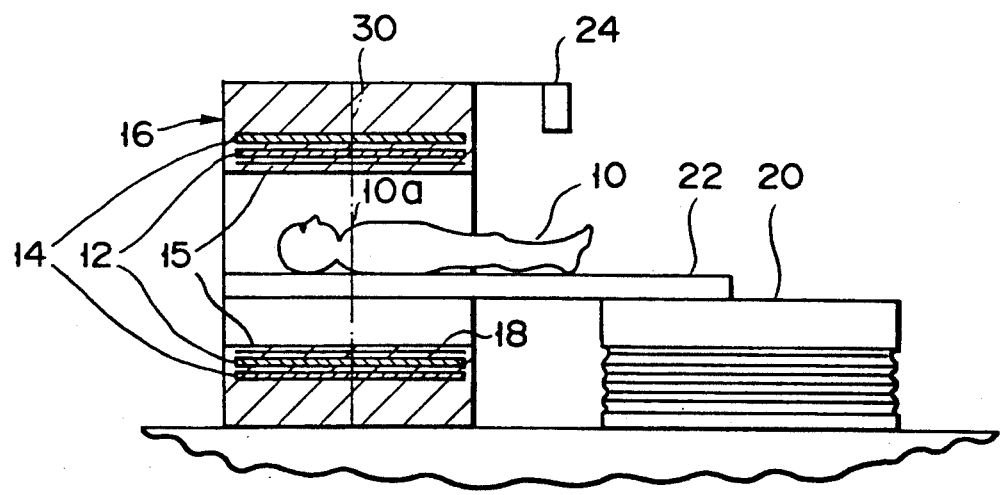
FIG. 2 is a side view schematically showing a state in which the table top is automatically moved from the automatic alignment preparing position of FIG. 1 until the inspected portion of the patient on the table top is brought into coincidence with a predetermined inspecting position in a main coil of the apparatus.
Figure 3:
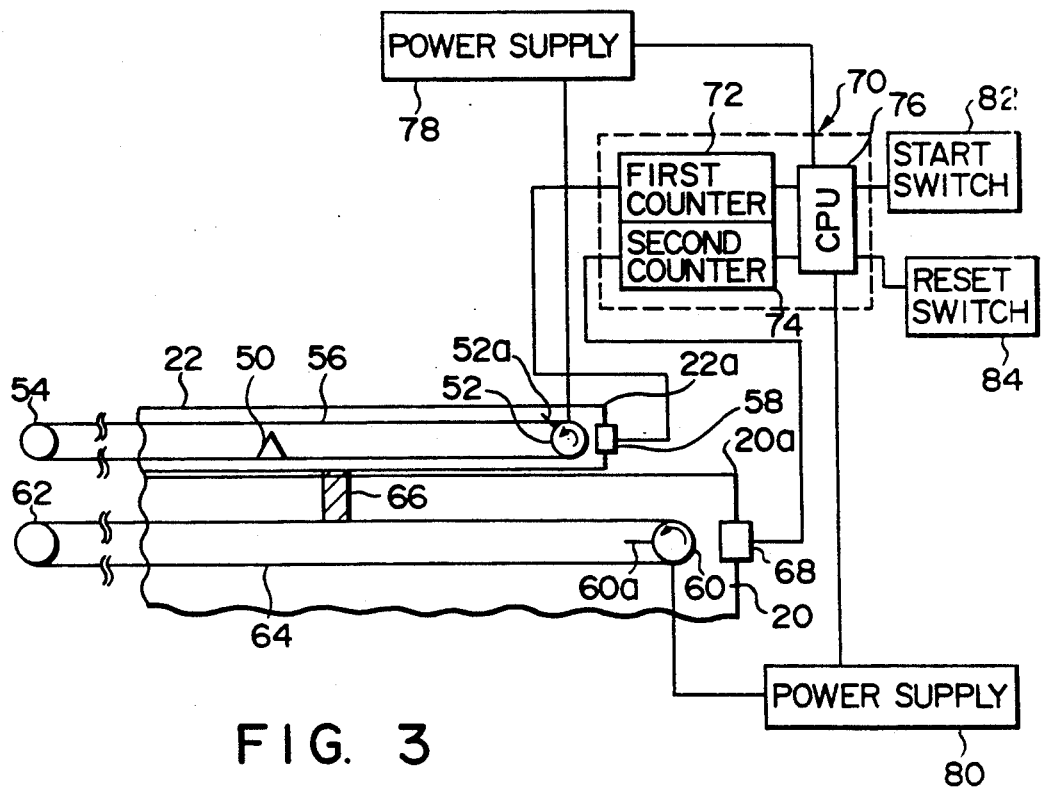
FIG. 3 is a side view schematically showing a automatic aligning mechanism for a nuclear magnetic resonance imaging apparatus, according to an embodiment of the present invention.
Figure 4:
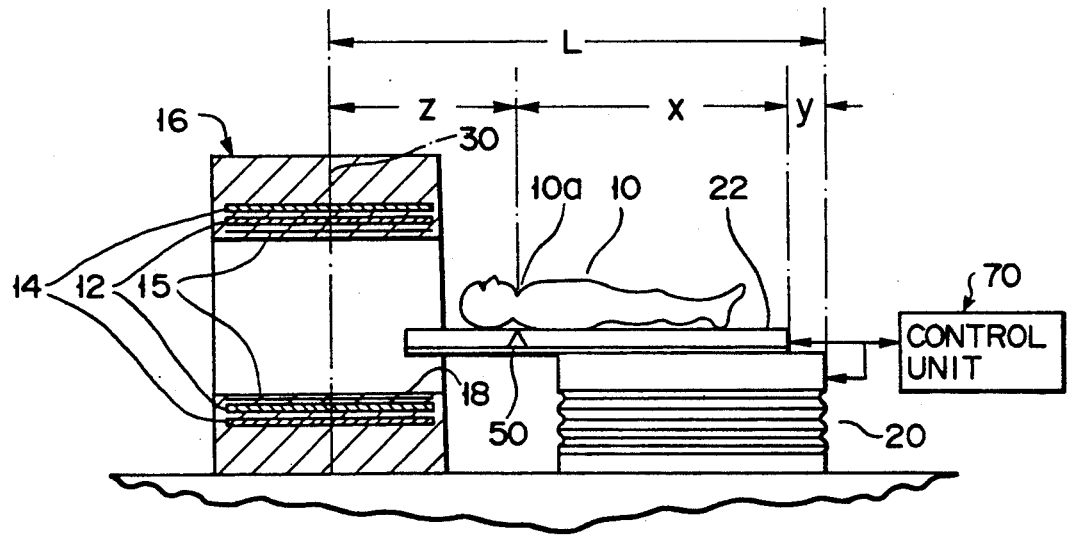
FIG. 4 is a side view schematically showing a state of non-stop movement of a table top of a bed of the mechanism in the automatic aligning mechanism of FIG. 3 while the table top, on which the patient is laid, is moved from an initial position to a predetermined inspecting position in a main coil of the apparatus, so that an inspected portion of the patient on the table top is brought into coincidence with the inspecting position.

In FIGS. 3 and 4, the same members as those in the automatic aligning mechanism for the above-mentioned conventional nuclear magnetic resonance imaging apparatus shown in FIGS. 1 and 2 are denoted by the same reference numerals, and the detailed description thereof will be omitted.

As shown in FIG. 3, an automatic aligning mechanism according to an embodiment of the present invention comprises an inspected-portion indicating member 50 which is movable along one of a pair of side surfaces (longitudinally extended side surfaces) extending in a moving direction of a table top 22 of a bed 20. A pair of rotational rollers 52 and 54 are rotatably disposed in the vicinity of one the above described side surfaces at both end portions of the table top 22 in the moving direction, and the inspected-portion indicating member 50 is secured to a flexible belt 56 hung over the pair of rollers 52 and 54.

A first photosensor 58 is disposed in the vicinity of one roller 52 in the table top 22, and the roller 52 has a photosensed member 52a passing the sensing region of the first photosensor 58 upon rotation of the roller 52.

A pair of rotary rollers 60 and 62 are rotatably supported in the vicinity of the table top 22 in a bed 20 at the both end portions of the bed 20 in the moving direction. A flexible belt 64 is hung over the pair of rollers 60 and 62, and the table top 22 is coupled to the flexible belt 64 through a coupling member 66.

A second photosensor 68 is disposed in the vicinity of one roller 60 in the bed 20, and the roller 60 has a photosensed member 60a passing a sensing region of the second photosensor 68 upon rotation of the roller 60.

The first and second photosensors 58 and 68 are respectively connected to first and second counters 72 and 74 contained in a control unit 70 for moving the table top 22 toward an opening 18 of a gantry 16 relative to the bed 20 for a distance having a predetermined relationship to the moving distance of the inspected-portion indicating member 50 from a predetermined initial position on the table top 22. The first and second counters 72 and 74 are connected to a CPU 76 in the control unit 70. The control unit 70 is further connected with a first power supply 78 such as a motor connected to one roller 52 for the inspected-portion indicating member 50 and a second power supply 80 such as a motor connected to one roller 60 for the table top 22. The control unit 70 is also connected with a start switch 82 and a reset switch 84 provided on the bed 20.

In the automatic aligning mechanism of the embodiment constructed as described above, a position where one end surface 22a of the table top 22 is remote from the gantry 16, and one end surface 20a of the bed 20 is from the gantry 16 is defined as an initial position of the table top 22 relative to the bed 20. The patient 10 rides on or get down from the table top 22 while the table top 22 is located at the initial position.

The initial position of the inspected-portion indicating member 50 relative to the table top 22 is a position where the inspected-portion indicating member 50 is brought into coincidence with the end surface 22a of the table top 22 remote from the gantry 16.

After the patient 10 is being laid at a predetermined position on the table top 22 in a state directed upward, and the table top 22 is being located substantially at the center in the vertical direction of the opening 18 of the gantry 16, the inspected-portion indicating member 50 is manually moved at first along a side surface of the table top 22 to a position corresponding to the inspected portion 10a of the patient 10. In the meantime, the rotational power source 78 connected to one roller 52 for the inspected-portion indicating member 50 is idly rotated.

The movement of the inspected-portion indicating member 50 causes one roller 52 for the inspected-portion indicating member 50 to rotate through a belt 56. The number of revolutions of the roller 52 is counted by the first counter 72 of the control unit 70 by utilizing the first photosensor 58, and a moving distance X (FIG. 4) of the inspected-portion indicating member 50 from the initial position is input to the CPU 76 of the control unit 70.

Here, the CPU 76 calculates a value, as a distance Z from the inspected portion 10a of the patient 10 on the table top 22 to the inspecting position 30 in the gantry 16, obtained by subtracting a total sum of the the above-described moving distance X and a distance Y of the table top 22 moved for the initial position relative to the bed 20 from a distance L (FIG. 4) from the initial position of the table top 22 to the inspecting position 30 in the gantry 16 input in advance.

The relationship among the values X, Y and Z can be represented by the following equation:

$$Z = L - (X + Y)$$

Since the table top 22 is normally stopped at the initial position with respect to the bed 20 at this stage, $Y=0$ is satisfied.

When the start switch 82 is then turned on, the CPU 76 rotates one roller 60 by the rotational power source 80 connected to one roller 60 for the table top 22, and moves the table top 22 toward the opening 18 of the gantry 16 until the value of the distance Z becomes zero. The moving distance Y of the table top 20 is input to the CPU 76 of the control unit 70 by counting the number of revolutions of one roller 60, rotated through the coupling member 66 and the belt 64 upon movement of the table top 22, by means of the second counter 72 of the control unit 70 through the second photosensor 68.

When the movement of the table top 22 controlled by the CPU 76 is automatically stopped, the inspected portion 10a of the patient 10 on the table top 22 is located at the inspecting position 30 in the gantry 16.

A predetermined operation necessary to produce a nuclear magnetic resonance image of a section of the inspected portion 10a of the patient 10 is then performed by the nuclear magnetic resonance imaging apparatus.

After the nuclear magnetic resonance image of the section of the inspected portion 10a of the patient 10 is obtained, the reset switch 84 connected to the CPU 76 of the control unit 70 is turned on. Thus, the CPU 76 rotates the rotational power source 80 for the table top 22 to move the table top 22 to the initial position, and rotates the power supply 78 connected to one roller 52 for the inspected-portion indicating member 50 until the inspected-portion indicating member 50 returns to the initial position.

When the reset switch 84 is turned on, the CPU 76 also clears the values of the first and second counters 72 and 74.

After the table top 22 is returned to the initial position, the patient 10 on the table top 22 may get down from the table top 22.

The above-described embodiment is for explaining the present invention, and the present invention is not limited to the particular embodiment. The present invention includes modifications and variations within the technical scope of the present invention.

For example, the inspected-portion indicating member 50 and the pair of rollers 52, 54, the flexible belt 56 and the first photosensor 58 may also be located in the vicinity of one side surface on the upper portion of the bed 20.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An automatic aligning mechanism for a nuclear magnetic resonance imaging apparatus including a gantry supporting a main coil, having a central space into which a subject is inserted, for generating a static magnetic field for said subject inserted into said central space, and supporting a gradient coil for generating a gradient magnetic field for producing position information of a portion of said subject induced with a nuclear magnetic resonance signal in said static magnetic field, said imaging apparatus producing an image of a section of said subject at a predetermined inspecting position in said central space of said main coil on the basis of said nuclear magnetic resonance signal from said portion of said subject, said mechanism comprising:
    a table top supporting base having a table top on which said subject is placed and which is movable to move said subject into and out from an opening of said gantry;
    means for measuring a position of an inspected portion of said subject on said table top, wherein said position measuring means includes an inspected-portion indicating member movable along a longitudinal side edge of said table top;
    indicating-member-moving-distance measuring means for measuring a moving distance of said inspected-portion indicating member from a predetermined initial position; and
    means for detecting a distance between an inspected portion of said subject and a predetermined inspecting position in said central space of said main coil on the basis of a measured result by said position measuring means, and for moving said table top for a detected distance toward said opening of said gantry.

2. A mechanism according to claim 1, wherein said indicating-member-moving-distance measuring means comprises:
    rotary means rotating in response to movement of said inspected-portion indicating member, and
    calculating means for calculating said moving distance of said inspected-portion indicating member in response to a rotating angle of said rotary means.

3. A mechanism according to claim 2, wherein said calculating means comprises a photosensor for detecting said rotating angle.

4. A mechanism according to claim 2, wherein
said rotary means comprises a pair of rotary members disposed at both end positions in the moving direction of said table top, and
said indicating-member-moving-distance measuring means further comprises an elongated flexible member hanging over said pair of rotary members and fixed to said inspected-portion indicating member,
said movement of said inspected-portion indicating member rotating said pair of rotary members through said flexible member.

5. A mechanism according to claim 1, wherein said table top supporting base comprises:
    table top moving control means including means for moving said table top, and
    means for measuring a moving distance of said table top from a predetermined initial position of said table top by said table top moving means;
    said initial position of said table top and an initial position of said inspected-portion indicating member being set to the same point, and
    said table top moving control means controlling said table top so that said table top moves toward said opening of said gantry until said moving distance of said table top measured by said table-top-moving-distance measuring means becomes equal to a distance between said inspected-portion of said subject and a predetermined inspecting position in said central space of said main coil.

6. A mechanism according to claim 5, wherein said table-top-moving-distance measuring means comprises:
    rotary means rotating in response to movement of said table top, and
    calculating means for calculating a moving distance of said table top in response to a rotating angle of said rotary means.

7. A mechanism according to claim 6, wherein said calculating means comprises a photosensor for detecting said rotating angle.

8. A mechanism according to claim 6, wherein said indicating-member-moving-distance measuring means comprises:
    rotary means rotating in response to movement of said inspected-portion indicating member, and
    calculating means for calculating said moving distance of said inspected-portion indicating member in response to said rotating angle.

9. A mechanism according to claim 8, wherein
said calculating means comprises a photosensor for detecting said rotating angle.

10. A mechanism according to claim 8, wherein
said rotary means comprises
    a pair of rotary members disposed at positions isolated from each other in a moving direction of said table top, and
    an elongated flexible member hanging over said pair of rotary members and fixed to said inspected-portion indicating member;
said movement of said inspected-portion indicating member rotates said pair of rotary members through said flexible member.

11. A mechanism according to claim 6, wherein
said rotary means comprises
    a pair of rotary members disposed at positions isolated from each other in a moving direction of said table top, and
    an elongated flexible member hanging over said pair of rotary members and fixed to said table top;
said movement of said table top rotates said pair of rotary members through said flexible member.

12. A mechanism according to claim 11, wherein
a rotational power source is coupled to one of said pair of rotary members.

* * * * *